United States Patent [19]

Supp et al.

[11]  4,203,915
[45]  May 20, 1980

[54] PROCESS OF PRODUCING METHANOL

[75] Inventors: Emil Supp, Dietzenbach; Heinz Jockel, Klein-Gerau; Hagen Krumm, Frankfurt am Main; Friedemann Marschner, Oberursel, all of Fed. Rep. of Germany

[73] Assignee: Metallgesellschaft, Frankfurt, Fed. Rep. of Germany

[21] Appl. No.: 945,727

[22] Filed: Sep. 25, 1978

Related U.S. Application Data

[63] Continuation-in-part of Ser. No. 850,565, Nov. 11, 1977, abandoned, which is a continuation of Ser. No. 724,031, Sep. 17, 1976, abandoned.

[30] Foreign Application Priority Data

Jan. 29, 1976 [DE] Fed. Rep. of Germany ....... 2603204

[51] Int. Cl.$^2$ ..................... C07C 31/04; C07C 31/06
[52] U.S. Cl. .................................. 260/449.5; 252/373
[58] Field of Search ....................... 260/449.5; 252/373

[56] References Cited

U.S. PATENT DOCUMENTS

| | | | |
|---|---|---|---|
| 2,944,627 | 7/1960 | Skarstron | 260/451 |
| 3,763,205 | 10/1973 | Green | 252/373 |
| 3,940,428 | 2/1976 | Connell et al. | 260/449.5 |

FOREIGN PATENT DOCUMENTS

| | | | |
|---|---|---|---|
| 2603204 | 8/1977 | Fed. Rep. of Germany | 260/449.5 |
| 42-15376 | 8/1967 | Japan | 252/373 |
| 1132776 | 11/1968 | United Kingdom | 252/373 |
| 1159035 | 7/1969 | United Kingdom | 260/449.5 |
| 1190071 | 4/1970 | United Kingdom | 260/449.5 |
| 1196038 | 6/1970 | United Kingdom | 252/373 |

OTHER PUBLICATIONS

Hersh, Molecular Sieves, Reinhold Publishing Corp., New York (1961), pp. 66, 79, 110–111.

*Primary Examiner*—Howard T. Mars
*Attorney, Agent, or Firm*—Sprung, Felfe, Horn, Lynch & Kramer

[57] ABSTRACT

In the production of methanol from gaseous and liquid hydrocarbons having a higher C/H ratio than is stoichiometrically required to produce methanol, wherein said hydrocarbons are catalytically cracked in the presence of water vapor and at a temperature of about 350°–950° C. and under a pressure of about 5–30 bars to produce a synthesis gas containing hydrogen and oxides of carbon, followed by a catalytic reaction of the hydrogen with the oxides of carbon at a temperature of about 230°–280° C. and under a pressure of about 30–150 bars to produce methanol, the improvement which comprises treating the methanol synthesis exhaust gas so as to remove therefrom carbonaceous gaseous constituents so that the residual gas is high in hydrogen, and adding said high-hydrogen residual gas to the hydrocarbons prior to cracking in an amount such that the C/H ratio of the material to be cracked is up to about 5.7, thereby reducing the energy consumption per unit of methanol produced. Advantageously, the cracking of said hydrocarbons is effected in two stages, the carbonaceous gaseous constituents removed from the methanol synthesis exhaust gas being used for indirect heating of the second cracking stage. The removal of the carbonaceous gaseous constituents from the methanol synthesis exhaust gas is effected by contacting such exhaust gas with a molecular sieve, at least part of the high-hydrogen residual gas being added to the hydrocarbons before the second stage, the mixture of hydrocarbons and high-hydrogen residual gas being treated to effect hydrogenation and desulfurization of the hydrocarbons.

3 Claims, 2 Drawing Figures

PROCESS OF PRODUCING METHANOL

This application is a continuation-in-part of application Ser. No. 850,565, filed Nov. 11, 1977, now abandoned, which is a continuation of application Ser. No. 724,031, filed Sept. 17, 1976, now abandoned.

This invention relates to a process of producing methanol from gaseous and liquid hydrocarbons having a higher C/H ratio than is stoichiometrically required to produce methanol, in which said hydrocarbons are catalytically cracked in one or two stages in the presence of water vapor and at temperatures of 350°–950° C. and under pressures of 5–30 bars to produce a synthesis gas which substantially consists of hyrogen and oxides of carbon, followed by a catalytic reaction of hydrogen with oxides of carbon at temperatures of 230°–280° C. and under pressures of 30–150 bars to produce methanol.

It is known that from a synthesis gas which contains hydrogen and oxides of carbon and has been produced by a cracking of hydrocarbons in the presence of water vapor in contact with an indirectly heated, nickel-containing catalyst at temperatures above 700° C, methanol can be produced in that said synthesis gas is reacted in contact with a copper-containing catalyst under pressures of 30–80 kg/cm² and at temperatures of 230°–280° C. The catalyst is arranged in tubes, which are indirectly cooled with water. The cooling of the reactor tubes results in the generation of high-pressure steam with utilization of the heat of reaction generated by the production of methanol (German Patent Specification No. 2,013,297).

It is also known to subject the hydrocarbons to a preliminary cracking without a supply of heat in a first stage in the presence of water vapor and in contact with a high-nickel catalyst at temperatures of 350°–500+ C. and under pressures of 1–30 bars whereby mixed gases are produced which contain about 60% methane, 20% $CO_2$ and 20% $H_2$ by volume, to re-crack said mixed gases in a second stage in known manner as described hereinbefore so as to form a methanol synthesis gas, and to produce methanol from said synthesis gas (company publication LURGI INFORMATION "The Lurgi Pressure Methanol Process, 01106/4.74", particularly page 3; Lurgi Mineralöltechnick GmbH, Gervinus-straBe 17–19, Frankfurt-on-Main).

This state of the art requires that the C/H ratio of the hydrocarbons to be cracked does not exceed 5.6 so that the ratio $(H_2-31 CO_2)/(CO+CO_2)$ has at least the value of 2.0 required for a synthesis of methanol.

When hydrocarbons having a C/H ratio above 5.6 are cracked, the ratio $(H_2-CO_2)/(CO+CO_2)$ will necessarily be lower than 2.0 so that part of the oxides of carbon must be removed from the methanol synthesis gas in order to increase the ratio $(H_2-CO_2)/(CO+CO_2)$ to at least 0.2.

To meet this requirement it is known to adjust a methanol synthesis gas consisting of carbon monoxide and hydrogen to the required ratio in that carbon dioxide is partly scrubbed off with methanol under superatmospheric pressure (German Patent Specification No. 1,262,987).

These proceses involve a high energy consumption and have the further disadvantage that the catalytic cracking of hydrocarbons having a C/H ratio above 5.6 is rendered more difficult by an increased content of high-boiling, particularly aromatic hydrocarbons and requires catalyst volumes and hydrogen rates which are much larger than those conventionally employed for a hydrogenating desulfurization of the hydrocarbons.

It is an object of the invention to avoid these and other disadvantages of the state of the art and to provide a process which permits production of methanol from gaseous and liquid hydrocarbons having a C/H ratio which is higher than stoichiometrically required to produce methanol. Specifically, the need for an expensive removal of oxides of carbon from the methanol synthesis gas should be eliminated.

For this reason it has been specifically desired to develop a process by which carbon oxides, particularly $CO_2$, can be removed without a consumption of energy.

This object is accomplished according to the invention in that, in order to reduce the thermal-/energy consumption per unit of the methanol product, carbonaceous gaseous constituents are removed from the methanol synthesis exhaust gas and the remaining, high-hydrogen gaseous constituents are admixed with the hydrocarbons to be cracked so as to provide a mixture having a C/H ratio up to 5.7.

According to a preferred feature of the invention, the catalytic cracking of the hydrocarbons is effected in two stages and part of the high-hydrogen gaseous constituents is mixed with the hydrocarbons before the second catalytic cracking stage.

According to a preferred feature of the invention, the carbonaceous gaseous constituents are removed from the exhaust gas without consumption of energy.

Within the scope of the invention, the carbonaceous gaseous constituents are preferably removed from the exhaust gas by a molecular sieve.

According to a further feature of the invention all or part of the high-hydrogen gaseous constituents are used for a hydro-generating desulfurization of the hydrocarbons to be cracked.

Within the scope of the invention, carbonaceous gaseous constituents are $CO_2$, CO, and/or $CH_4$.

According to another preferred feature of the invention the carbonaceous gaseous constituents are used for an indirect heating in a second catalytic cracking stage.

The advantages afforded by the invention reside particularly in that methanol can be produced in a simple and economical manner even from hydrocarbons having a C/H ratio which is higher than stoichiometrically required to produce methanol. In accordance with the invention, carbonaceous gaseous constituents are removed, preferably without any consumption of energy, from the methanol synthesis exhaust gas so that a high-hydrogen gas is obtained, which is admixed at such a rate with the hydrocarbons to be cracked that the resulting mixture has a C/H ratio up to 5.7, as is required for a synthesis of methanol. These measures result in a much lower thermal-/energy consumption per unit of the methanol product. Within the scope of the invention, part of the high-$H_2$ gas may be admixed before and/or after a second catalytic cracking stage. An additional advantage afforded by the process resides in the alleviation or suppression of the action of certain hydrocarbons, such as aromatic compounds, which are contained in the feedstocks and can be reacted only with difficulty in contact with the nickel catalyst used in the two catalytic cracking stages. As a result, the catalyst which is employed is much less adversely affected and has a long useful life. This enables also the use of a smaller amount of catalyst than has been usual before when the efficiency and end product yield are the same in other respects.

A further advantage afforded by the process according to the invention resides in that it can be used for processing sulfur-containing feedstocks. In this case, the high-hydrogen gaseous constituents my be used in the process for hydrogenating desulfurization of the hydrocarbons to be cracked. Within the scope of the invention, the carbonaceous gaseous constituents, which have been removed, e.g., by molecular sieves, may be used as an additional energy source, e.g., for an indirect heating in the second catalytic cracking stage. This has the advantage that virtually all substances are utilized and polluting exhaust gases are not formed at all. For this reason the process according to the invention is highly satisfactory from an ecologic aspect.

The invention will be further described with reference to the accompanying drawings, wherein.

Figure 1:
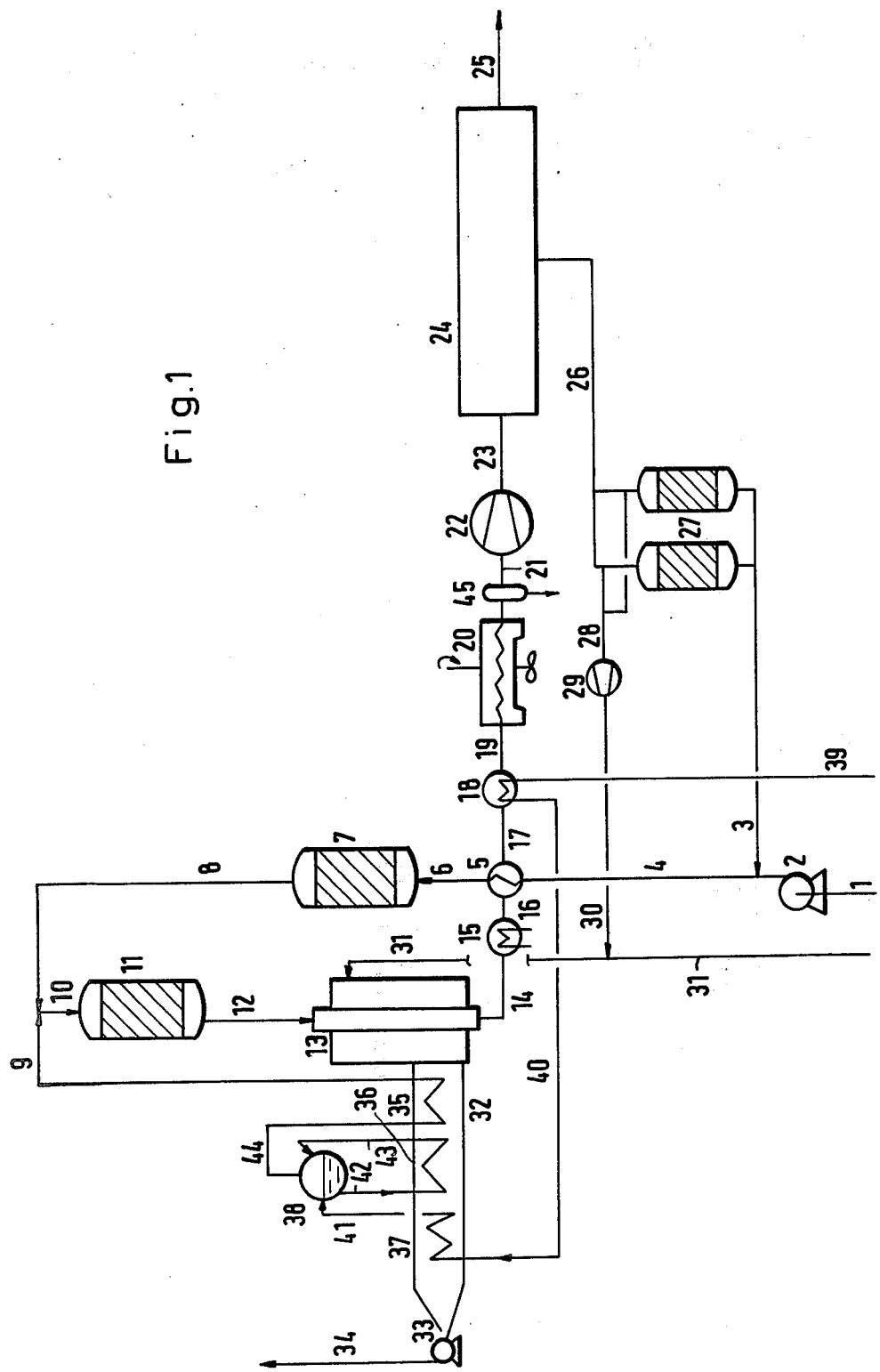
FIG. 1 is a diagrammatic view showing by way of example the process according to the invention with an admixing of the high-hydrogen gaseous constituents at only one point.

The process according to the invention is carried out as follows:

The hydrocarbon feedstock, such as naphtha, flows in conduit 1 to a pump 2, in which it is pressurized to the required process pressure. A high-hydrogen gas from a molecular sieve installation 27 is fed through conduit 3 to the naphtha. The naphtha-hydrogen mixture flows in conduit 4 to an evaporator-superheater 5, which will be referred to hereinafter as naphtha evaporator-superheater, and is superheated therein to 350° C. and subsequently fed in conduit 6 to a desulphurizing stage 7, in which the hydrocarbon, such as naphtha, is subjected to a hydrogenating desulfurization.

The desulfurized naphtha-hydrogen mixture is withdrawn in conduit 8, mixed with the superheated steam of about 450° from conduit 9, and fed in conduit 10 to a rich gas reactor 11, which is filled with a high-activity nickel catalyst and in which the naphtha-hydrogen mixture reacts with the added process steam. The temperature in the reactor rises from about 380°-400° C. at the inlet to about 480° C. at the outlet of the reactor.

The gas leaving the rich gas reactor 11 contains mainly $CH_4$, also $H_2$ and $CO_2$ as well as process steam which has not been decomposed. CO is present only in small quantities. This gas is supplied in conduit 12 to a tubular heater 13 which contains tubes which are externally heated from a furnace and are filled with a suitable nickel catalyst. The gas enters these tubes and is further reacted therein.

The heating causes the temperature of the catalyst at the outlet to be maintained at 800°-950° C. The gas produced in the tubular heater 13 has high hydrogen and CO contents and a low residual methane content. When the gas has been cooled with condensation of the residual process steam that has not been decomposed, the gas can be used as methanol synthesis gas.

The tubular heater 13 is indirectly heated by a burner system, which is suppled with fuel from the outside through conduit 31. Exhaust gas from the molecular sieve installation 27 is also fed through conduit 30 for a supply of heat.

Cracked gases leave the tubular heater at 850°-950° C. and are conducted in conduit 14 to a steam-generating waste heat boiler 15 and are cooled therein and are then fed in conduit 16 to the above mentioned naphtha evaporator-superheater 5. The gas is fed in conduit 17 to a feed water heater 18 and is further cooled therein. Boiler feed water enters the plant through a conduit 39 under the required pressure and is preheated in the feed water heater 18. The cracked gases are then fed in conduit 19 to an air cooler 20, in which the heat which cannot be utilized is dissipated. Condensate is formed as the temperature drops below the dew point of water vapor and is separated in a separator 45. The synthesis gas at a low temperature of about 40° C. is fed in conduit 21 to a compressor 22, compressed to synthesis pressure and fed in conduit 23 to a methanol synthesizer 24. Raw methanol produced in the methanol synthesizer 24 is withdrawn through conduit 25.

High-hydrogen exhaust gas, which contains also CO, $CO_2$, $CH_4$, and small amounts of methanol, is withdrawn through conduit 26 and passed through a molecular sieve installation 27, which consists of a plurality of adsorbers and in which all gaseous constituents other than hydrogen are adsorbed.

Figure 2:
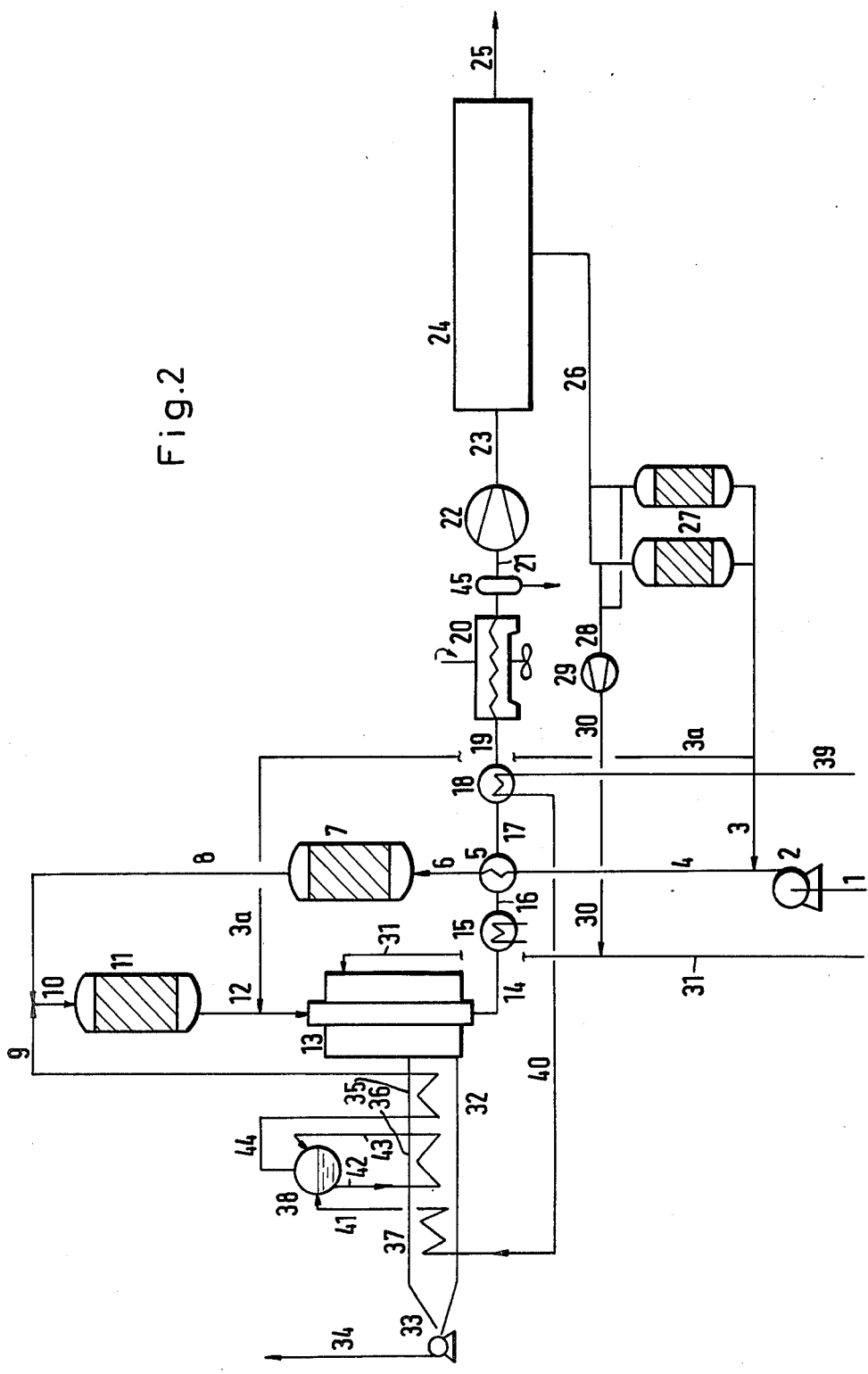
FIG. 2 illustrates a further development of the invention, in which the high-hydrogen gaseous constituents are divided and are admixed at two points with the hydrocarbons to be cracked.

The compressed high-hydrogen gas which becomes available is fed in conduit 3 to the feedstock, such as naphtha, flowing in conduit 4. Depending on the composition of the naphtha feedstock it may be necessary to introduce part of the high-hydrogen gas through 3a into the outlet conduit 12 of the rich gas reactor 11, as shown in FIG. 2. This will be required if the addition of hydrogen to the naptha in conduit 4 results in an excessively high temperature rise in the rich gas reactor 11 because an addition of more hydrogen to the naphtha will result in a larger heat effect in the rich gas reactor 11.

When an adsorber of the molecular sieve installation 27 has been laden, the adsorber is regenerated in that it is pressure-relieved to a slightly superatmospheric pressure so that a major part of the adsorbed gases escapes. For a further regeneration, part of the hydrogen now produced in another adsorber is passed through the previously used adsorber to carry off the remaining adsorbed gases. The exhaust gases from the molecular sieve installation are fed in conduit 28 to a compressor 29 and compressed therein and are then fed as fuel gas in conduit 30 to the tubular heater 13.

The hot flue gases from the tubular heater are withdrawn through a flue gas duct 32 and are cooled in various heat exchangers and then blown in the atmosphere through a chimney 34 by a flue gas blower 33. To cool the flue gases from the tubular heater 13, the boiler feed water which has been preheated in the heat exchanger 18 is fed through conduit 40 to a heat exchanger 37 and is further heated therein and subsequently fed through conduit 41 into a steam drum 38. From the steam drum, the boiler water flows through a conduit 42 to a flue gas waste heat boiler 36 and is partly evaporated. The steam-water mixture is fed in conduit 43 back to the boiler drum 38, in which the water and steam phases are separated. The steam generated in the plant flows in conduit 44 to a superheater and is added as process steam through conduit 9 to the desulfurized naphtha before the rich gas reactor 11.

The invention is further described in the following illustrative examples.

EXAMPLE 1

The hydrocarbon feedstock consists of a so-called "full-range" naphtha having the following specification: Initial boiling point 40° C., final boiling point 185° C., C/H ratio 6.0 kg/kg.

The naphtha feedstock at a rate of 1 kg/h is mixed with hydrogen at a rate of 0.4 standard m$^3$/h. The mixture is superheated to 350° C. under a pressure of 19 bars, and water vapor at a rate of 2.7 kg/h is admixed with the superheated mixture. The resulting mixture is fed to a first reaction vessel (rich gas reactor 11), which is filled with 0.5 liter of a high-activity nickel catalyst. The temperature of the admixed steam is so controlled that the mixture enters at a temperature of 380° C. The mixed gases leave the rich gas reactor 11 at 480° C. and under a pressure of 18.0 bars. They do not contain hydrocarbons other than methane and are fed to a tubular heater 13. The heat supply to the tubular heater 13 is so controlled that the gas exits at a temperature of 865° C.

At a rate of 4.94 standard m$^3$/h, a gas having the following composition by volume (on a dry basis)

| | |
|---|---|
| $CO_2$ | 7.98% |
| $CO$ | 20.07% |
| $H_2$ | 67.63% |
| $CH_4$ | 4.32% | leaves the tubular heater 14 under a pressure of 15 bars. This gas still contains 0.32 standard m$^3$ water vapor per standard cubic meter of gas.

The quotient $(H_2-CO_2)/(CO+CO_2)$ equals 2.13.

The gas is suitable as a methanol synthesis gas. It is cooled, compressed, and fed to a methanol synthesizer 24, in which 1.75 kg methanol are produced per hour. The synthesis is carried out under a pressure of 50 bars and at a temperature of 250° C.

The exhaust gas which becomes available in the methanol synthesizer 24 under a pressure of about 48 bars contains 62.0% hydrogen by volume. To recover the hydrogen added to naphtha, this exhaust gas is pressure-relieved to 25 bars and is then passed through a molecular sieve installation 27, which consists of a plurality of adsorbers and in which all gaseous constituents other than hydrogen, such as $CH_4$, $CO_2$, and $CO$, are adsorbed. An adsorber which has been laden with contaminating gaseous constituents is pressure-relieved to atmospheric pressure so that a large part of the adsorbed gases is desorbed. For further regenerating, the adsorber is subsequently purged with part of the pure hydrogen then produced in another adsorber. No energy is required for the recovery of hydrogen in the molecular sieve installation 27.

The experimental operation was discontinued after 1300 hours, in which there has been no trouble. The nickel catalysts were removed from both reaction vessels and were satisfactory in appearance.

CONTROL EXAMPLE 2

For a comparison with the example of the process according to the invention, a control experiment was carried out, in which the same hydrocarbon feedstock and the same operating conditions were employed.

Naphtha having the same specification as in the example was fed at 1 kg/h and superheated to 350° C. under a pressure of 19.0 bars. Water vapor 2.7 kg/h was admixed with the superheated naptha. The resulting mixture was fed into a first reaction vessel (rich gas reactor 11), which was filled with 0.5 liter of a high-activity nickel catalyst. The temperature of the added steam was so controlled that the mixture entered at 400° C. Mixed gases containing no hydrocarbons other than methane exited from the rich gas reactor 11 at 480° C. and under a pressure of 18.0 bars and were fed to a second reaction vessel (tubular heater 13), which was filled with a nickel catalyst, which was maintained at a high temperature by indirect heating. The heat supply to the tubular heater was so controlled that the gas exited at 865° C.

At a rate of 4.65 standard m$^3$/h, a gas having the following composition by volume (on a dry basis)

| | |
|---|---|
| $CO_2$ | 9.02% |
| $CO$ | 21.38% |
| $H_2$ | 65.57% |
| $CH_4$ | 4.03% | left the tubular heater under a pressure of 15.0 bars. This gas still contained 0.33 standard m$^3$ of undecomposed water vapor per standard m$^3$ of gas.

The quotient $(H_2-CO_2)/(CO+CO_2)$ equalled 1.86. With that composition the gas was not suitable for a synthesis of methanol.

To enable the use of this gas for the synthesis of methanol, the above quotient had to be increased to at least 2.05 by a decrease of the $CO_2$ content of the gas. For this purpose the gas leaving the tubular heater 13 was cooled to 120° C. and passed through an absorber ($CO_2$ scrubber) which was fed with hot potash (potassium carbonate) solution and in which 0.09 standard m$^3$ $CO_2$ was scrubbed off per hour.

At a rate of 4.56 standard m$^3$/h, a water vapor-saturated gas having the following composition by volume (on a dry basis)

| | |
|---|---|
| $CO_2$ | 7.27% |
| $CO$ | 21.79% |
| $H_2$ | 66.83% |
| $CH_4$ | 4.11% | left the absorber at 100° C. and under a pressure of 14 bars. The quotient $(H_2-CO_2)/(CO+CO_2)$ equalled 2.05.

The hot potash solution was pressure-relieved to 1 bar in a regenerator and was reboiled by being indirectly heated with low-pressure saturated steam supplied at 0.2 kg/h to release the adsorbed carbon dioxide. 7 watts of electric power were required to return the thus regenerated solution to the adsorber by a pump.

The gas leaving the $CO_2$ scrubber was cooled and compressed and was then fed to a methanol synthesizer 24, in which 1.65 kg methanol were produced per hour. The synthesis was carried out under a pressure of 50 bars and at a temperature of 250° C.

The experiment had to be discontinued after 700 hours because the insufficient conversion in the rich gas reactor caused naphtha to enter the tubular heater together with the gas from the rich gas reactor and said naphtha was decomposed in the tubular heater with formation of carbon black and a pressure loss increased by several bars.

EXAMPLE 3

The process of Example 1 is repeated, the catalyst in the rich gas reactor 11 consisting of nickel on a magnesium silicate carrier, the nickel constituting 40% of the total weight. The catalyst in the tubular heater 13 consists of nickel on α-alumina as carrier, the nickel constituting 12% of the total weight. The catalyst in the methanol synthesizer 24 consists of 60 atom % Cu, 30 atom % Zn and 10 atom % V, as described in U.S. Pat. No. 3,897,471.

The exhaust gas leaving synthesizer 24 through conduit 26 has the following compositon by volume:

| | |
|---|---|
| $CO_2$ | 8.02% |
| CO | 6.94% |
| $H_2$ | 61.87% |
| $CH_4$ | 22.57% |
| $H_2O$ | 0.03% |
| $CH_3OH$ | 0.57% |

This gas, at the rate of 0.9 standard m³ per hour, is supplied to a pressure swing adsorber molecular sieve installation 27 consisting of four adsorption units filled with synthetic crystalline aluminosilicate sold by Union Carbide under the trademark "HYSIV type H2". Every adsorption unit operates cyclically and adiabatically. Each cycle consists of the four steps (1) adsorption, (2) depressurizing, (3) flushing and (4) pressurizing.

While, e.g. the first unit is being used for adsorption, the other three are undergoing regeneration. Specifically, the second unit has finished adsorption and is depressurized, the third unit is flushed under low pressure with part of the hydrogen product from the first unit, and the fourth unit, which is already flushed, is pressurized with the depressurizing gas from the second unit. Every unit is cyclically put in operation, viz. steps (1), (2), (3), (4), (1), etc. The gas from the depressurized and flushed units is at a low pressure and is fed by means of a compressor as fuel to the tubular heater 13.

The gas leaving synthesizer 24 has a pressure of 50 bars and the hydrogen leaving installation 27 has a pressure of 25 bars. Technically pure hydrogen leaves installation 27 at the rate of 0.4 standard m³ per hour. The gas at the rate of 0.5 standard m³/h removed from installation 27, which contains carbonaceous gaseous components and hydrogen from flushing, has the following composition by volume:

| | |
|---|---|
| $CO_2$ | 14.43% |
| CO | 12.48% |
| $H_2$ | 31.40% |
| $CH_4$ | 40.60% |
| $H_2O$ | 0.06% |
| $CH_3OH$ | 1.03% |

This gas is employed for fueling furnace 13, as described. It will be appreciated that the instant specification and examples are set forth by way of illustration and not limitation, and that various modifications and changes may be made without departing from the spirit and scope of the present invention.

What is claimed is:

1. In the production of methanol from gaseous and liquid hydrocarbons having a higher C/H ratio than is stoichiometrically required to produce methanol, wherein said hydrocarbons are catalytically cracked in the presence of water vapor and at a temperature of about 350°–950° C. and under a pressure of about 5–30 bars to produce a synthesis gas containing hydrogen and oxides of carbon, followed by a catalytic reaction of the hydrogen with the oxides of carbon at a temperature of about 230°–280° C. and under a pressure of about 30–150 bars to produce methanol, the improvement which comprises treating the methanol synthesis exhaust gas adiabatically in an adsorption unit filled with aluminosilicate molecular sieve so as to remove therefrom the carbonaceous gaseous constituents so that the residual gas is pure hydrogen, adding said hydrogen to the hydrocarbons prior to cracking in an amount such that the C/H ratio of the material to be cracked is up to about 5.7, and burning the carbonaceous gaseous constituents removed from the methanol synthesis exhaust gas by the molecular sieve as fuel for heating of the cracking catalyst thereby reducing the energy consumption per unit of methanol produced.

2. A process according to claim 1, wherein the cracking of said hydrocarbons is effected in two stages, at least part of the hydrogen being added to the hydrocarbons between the first and second stage.

3. A process according to claim 2, wherein the mixture of hydrocarbons and hydrogen is treated to effect hydrogenation and desulfurization of the hydrocarbons.